United States Patent
Li (10) Patent No.: US 9,677,951 B2
(45) Date of Patent: Jun. 13, 2017

(54) NON-INTRUSIVE PRESSURE SENSOR SYSTEM

(71) Applicant: Zhen Li, Houston, TX (US)

(72) Inventor: Zhen Li, Houston, TX (US)

(73) Assignee: ExxonMobil Upstream Research Company, Spring, TX (US)

(*) Notice: Subject to any disclaimer, the term of this patent is extended or adjusted under 35 U.S.C. 154(b) by 203 days.

(21) Appl. No.: 14/321,605

(22) Filed: Jul. 1, 2014

(65) Prior Publication Data

US 2015/0055679 A1  Feb. 26, 2015

Related U.S. Application Data (60) Provisional application No. 61/869,389, filed on Aug. 23, 2013.

(51) Int. Cl.

| | |
|---|---|
| G01L 7/00 | (2006.01) |
| G01K 13/02 | (2006.01) |
| G01L 7/02 | (2006.01) |
| E21B 47/12 | (2012.01) |
| G01L 9/00 | (2006.01) |
| E21B 47/00 | (2012.01) |
| E21B 47/06 | (2012.01) |
| A61B 5/0215 | (2006.01) |
| G01L 19/06 | (2006.01) |

(Continued)

(52) U.S. Cl.
CPC .......... *G01K 13/02* (2013.01); *E21B 47/0006* (2013.01); *E21B 47/06* (2013.01); *E21B 47/123* (2013.01); *G01L 7/026* (2013.01); *G01L 9/0032* (2013.01); *G01L 19/0023* (2013.01); *G01L 19/0092* (2013.01); *A61B 5/0215* (2013.01); *G01L 7/00* (2013.01); *G01L 19/0007* (2013.01); *G01L 19/04* (2013.01); *G01L 19/06* (2013.01)

(58) Field of Classification Search
CPC ........................................................ G01L 7/00
USPC .......................................................... 73/700
See application file for complete search history.

(56) References Cited

U.S. PATENT DOCUMENTS

| | | | |
|---|---|---|---|
| RE37,283 E | 7/2001 | Kluth et al. | |
| 6,957,588 B1 * | 10/2005 | Kicher | G01L 9/0002 73/720 |

(Continued)

FOREIGN PATENT DOCUMENTS

| | | | | |
|---|---|---|---|---|
| CA | 2638664 | * | 2/2010 | G01L 7/08 |
| DE | 27 30 509 | | 1/1979 | |

(Continued)

OTHER PUBLICATIONS

Hawk Measurement Systems, www.hawkmeasure.com, Fibre Optic Monitoring Solutions for Oil & Gas / Water Pipelines, May 18, 2007.*

(Continued)

*Primary Examiner* — Clayton E Laballe
*Assistant Examiner* — Kevin Butler
(74) *Attorney, Agent, or Firm* — ExxonMobil Upstream Research Company, Law Dept.

(57) ABSTRACT

A conduit pressure sensor system and a process for non-intrusively determining the pressure within a conduit. In one example, the sensor system has a base section having an external surface and an internal region in fluid connection with the conduit. A strain sensor and a temperature sensor are positioned adjacent to the external surface of the base section.

14 Claims, 5 Drawing Sheets

(51) Int. Cl.
*G01L 19/04* (2006.01)
*G01L 19/00* (2006.01)

(56) References Cited

U.S. PATENT DOCUMENTS

| | | | | |
|---|---|---|---|---|
| 7,703,331 | B2* | 4/2010 | Magne | E21B 43/01 73/766 |
| 7,926,579 | B2* | 4/2011 | Sbordone | E21B 33/076 166/346 |
| 8,111,952 | B2* | 2/2012 | Herbst | G01L 1/242 385/12 |
| 8,127,801 | B2 | 3/2012 | Brower | |
| 8,177,424 | B2* | 5/2012 | Hampson | G01K 1/14 374/131 |
| 8,402,834 | B1* | 3/2013 | Moslehi | G01L 9/0076 73/705 |
| 9,004,174 | B2* | 4/2015 | Mebarkia | E21B 41/0085 166/247 |
| 2004/0168521 | A1* | 9/2004 | Andersen | E21B 47/0006 73/807 |
| 2005/0100414 | A1* | 5/2005 | Salama | E21B 17/01 405/224.2 |
| 2005/0103123 | A1 | 5/2005 | Newman | |
| 2006/0074479 | A1* | 4/2006 | Bailey | A61B 5/076 623/1.13 |
| 2008/0148860 | A1* | 6/2008 | Murakami | G01L 9/0002 73/726 |
| 2008/0289431 | A1* | 11/2008 | Lohr | G01L 9/0002 73/703 |
| 2011/0219866 | A1 | 9/2011 | Brower | |
| 2012/0210793 | A1* | 8/2012 | Daton-Lovett | E21B 47/0001 73/570 |
| 2012/0211235 | A1 | 8/2012 | Smith | |
| 2013/0247675 | A1* | 9/2013 | Poissy | G01L 9/0002 73/716 |
| 2015/0226622 | A1* | 8/2015 | Cheng | G01L 9/0027 73/730 |

FOREIGN PATENT DOCUMENTS

| | | | | |
|---|---|---|---|---|
| DK | DE2730509 | * | 1/1979 | G01L 1/22 |
| GB | 757597 | * | 9/1956 | G01L 7/00 |

OTHER PUBLICATIONS

HBM measure and predict with confidence, Fiber Optic Strain Sensors Monitor Pipeline Integrity, Feb. 2, 1998.*
Mustapha et al., Stress Sensing by an Optical Fiber Sensor: Method and Process for teh Characterization of the Sensor Response Depending on Several Designs, Optics and Photonics Journal, Mar. 2013, 194-203.*
Wikipedia, the free encyclopedia, "Pressure Sensor", Wikipedia® is a registered trademark of the Wikimedia Foundation, Inc., a non-profit organization, last modified on Jan. 31, 2016, at 16:30.*
Offshore, Using Optical fibers for integrity monitoring in risers, flowlines, PennWell Corporation, Tulsa, OK, Apr. 1, 2009, pp. 1-7.*
Roberts, D., "Subsea Integrity Monitoring Using Fibre Optic Strain Sensors", 2007, Scandinavian Oil-Gas Magazine, No. 7/8, pp. 161-166.

* cited by examiner

NON-INTRUSIVE PRESSURE SENSOR SYSTEM

CROSS REFERENCE TO RELATED APPLICATIONS

This application claims the benefit of U.S. Provisional No. 61/869,389, filed Aug. 23, 2013, which is incorporated herein in its entirety for all purposes.

FIELD OF INVENTION

This invention generally relates to the field of pressure and temperature sensors and, more particularly, to non-intrusive sensor systems for use with pipelines, conduits and other vessels and methods for deploying and using the same.

BACKGROUND

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of prior art.

In conventional subsea production and processing systems, monitoring is typically done by means of subsea sensors. A majority of conventional monitoring systems utilize pressure-temperature (PT) sensors. Such sensors collect production parameters at each sensing point in real-time to provide information on system health condition. For subsea processing, such as, but not limited to, pumping, compression and separation, subsea PT sensors can provide control signals necessary for proper operation. As a result, sensor failure may result in extended unplanned shutdown of the subsea processing system resulting in production loss. For example, if the PT sensor on a subsea separator fails, the whole subsea separation system may have to be shut down because the control system cannot operate without the signal from the PT sensor. Therefore, subsea PT sensors are critical for subsea production; however, their reliability is often insufficient for subsea fields because sensor failures result in high intervention costs in addition to production losses.

Figure 1:
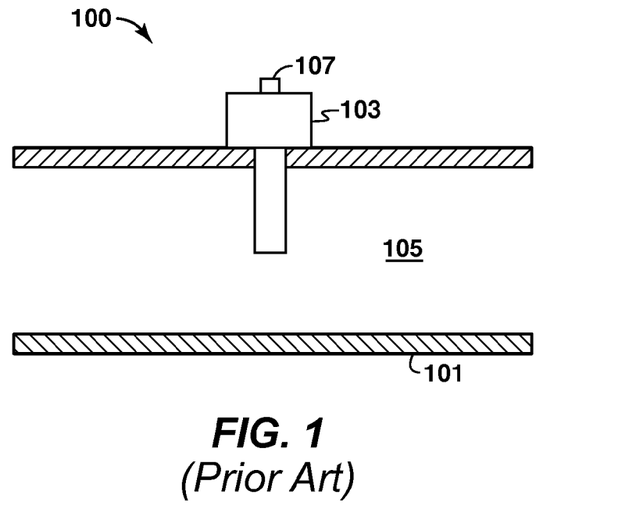
FIG. 1 is a cross-sectional side view of a pipeline sensor system as presently known in the prior art.

Conventional subsea PT sensors are not designed to be retrievable by a remotely operated vehicle (ROV). A monitoring system 100 is depicted in FIG. 1. System 100 includes a pipeline 101 which is designed to deliver product, such as, but not limited to, hydrocarbons in liquid or gaseous form, from one location to another. A sensor 103 is provided to monitor conditions within the interior region 105 of pipeline 101. Information collected by sensor 103 may be communicated to a control module or other known components via communication cable 107.

As depicted, a portion of sensor 103 is inserted through an aperture provided in pipeline 101. However, such a design is problematic. Sensor failures result in high intervention and repair costs in addition to production losses because the retrieval of a tree or production equipment is required to replace the failed sensor. To mitigate PT sensor failures, some known strategies call for ROV-installable external ("retrofit") strain gauges to be clamped onto the tree to replicate the function of the failed pressure sensors. One such known strain gauge technology is capable of detecting relative pressure with an accuracy of 10 psi. However, the pressure gauge only provides a relative pressure reading and is therefore not suitable for applications requiring absolute pressure readings such as processing control.

Thus, there is a need for improvement in this field.

SUMMARY OF THE INVENTION

The present invention provides conduit pressure sensor system.

One embodiment of the present disclosure is a system for non-intrusively determining pressure comprising a conduit; a base section having an external surface and an internal region in fluid connection with the conduit; a strain sensor positioned adjacent to the external surface of the base section; and a temperature sensor positioned adjacent to the external surface of the base section.

The foregoing has broadly outlined the features of one embodiment of the present disclosure in order that the detailed description that follows may be better understood. Additional features and embodiments will also be described herein.

BRIEF DESCRIPTION OF THE DRAWINGS

The present invention and its advantages will be better understood by referring to the following detailed description and the attached drawings.

It should be noted that the figures are merely examples of several embodiments of the present invention and no limitations on the scope of the present invention are intended thereby. Further, the figures are generally not drawn to scale, but are drafted for purposes of convenience and clarity in illustrating various aspects of certain embodiments of the invention.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 2:
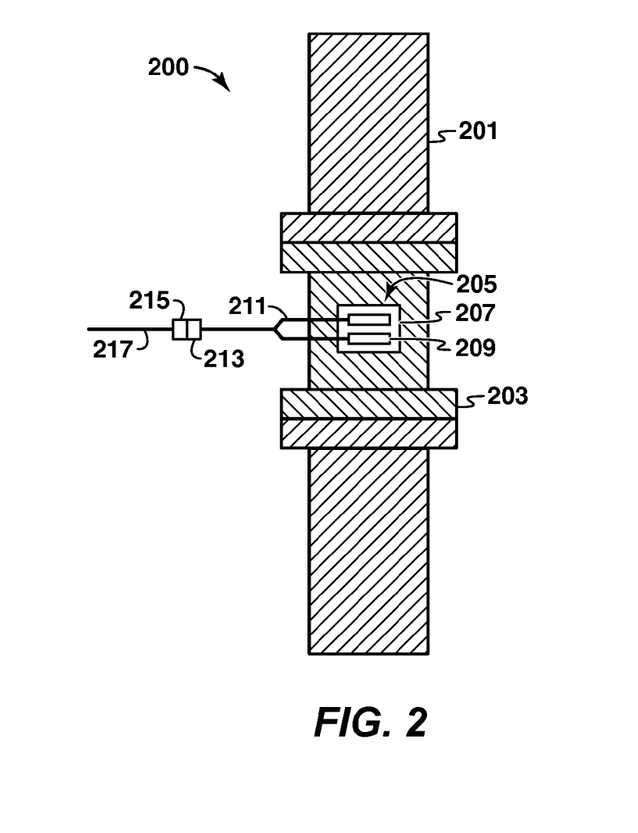
FIG. 2 is a top view of a pipeline sensor system according to one embodiment of the present disclosure.

FIG. 2 is a top view of a pipeline sensor system 200 according to one embodiment of the present disclosure. As depicted, system 200 contains a pipeline 201 and non-corrosive base section 203 which is provided a various locations along pipeline 201. As used herein, the term "pipeline" includes any line in which fluid is moved, including any onshore or offshore flow system, such as mainline systems, risers, flow lines used to transport untreated fluid between a wellhead and a processing facility, and flow lines used to transport treated fluids.

A sensor module 205 is provided on the exterior surface of non-corrosive base 203. Though discussed in more detail herein below, sensor module 205 includes a base or mounting portion 207 and at least one sensor component 209. Each sensor component 209 has a sensor cable 211 which terminate at connector 213. A data and communications cable 217 is connected to sensor module 205 via connector 215. Sensor component 209 may comprise fiber optic cable and/or sensors.

Figure 3:
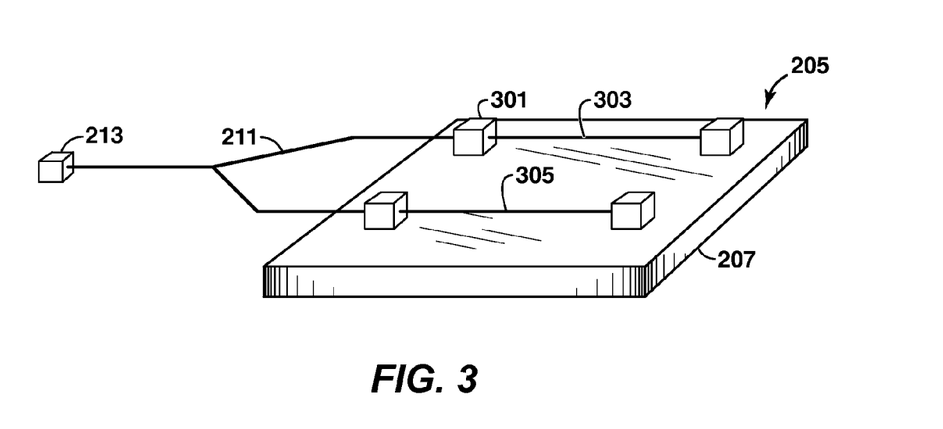
FIG. 3 is a perspective view of a fiber optic sensor according to one embodiment of the present disclosure.

FIG. 3 is a perspective view of sensor module 205 according to one embodiment of the present disclosure. As depicted, support structures 301 are mounted to base portion 207. Support structures 301 provide mechanical support for the fiber optic cables 303, 305. Support structures 301 may be mounted to base portion 207 through known means. The mechanisms and techniques used to connect the fiber optic sensing elements 303, 305 to support structures 301 and communicatively connecting sensor cables 211 to the respective fiber optic cables are well understood by those skilled in the art. Fiber optic sensing elements 303, 305 may be connected to base portion 207 through a variety of known techniques, such as, but not limited to, epoxy or spot welding.

Figure 4:
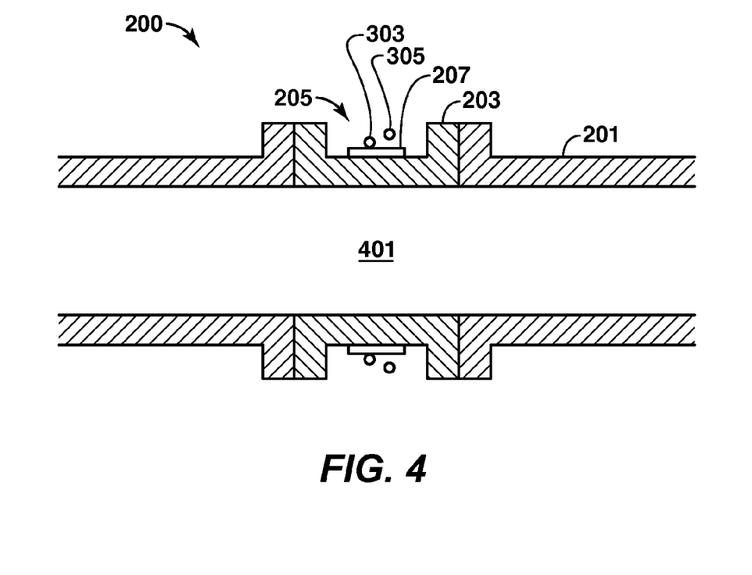
FIG. 4 is a cross-sectional side view of the pipeline sensor system depicted in FIG. 2.

FIG. 4 is a cross-sectional side view of the pipeline sensor system 200 depicted in FIG. 2. As depicted, the inner region of pipeline 201 is generally depicted by reference numeral 401. The non-corrosive base 203 may be constructed of a variety of materials, such as, but not limited to, titanium or other corrosion resistant alloys such as Alloy 13 Cr, Alloy S13 Cr, Alloy 316L, Alloy 22 Cr duplex, Alloy 25 Cr duplex, Alloy 28, Alloy 825, Alloy 2550, Alloy 625, Alloy C-276, which will not corrode in subsea or other harsh environments. Non-corrosive base 203 may be constructed and arranged to have a variety of different geometries. When non-corrosive base is not constructed to have a substantially circular cross-section, connections to pipeline 201 or vessel that needs PT measurement will vary accordingly. Base portion 207 may be connected to non-corrosive base 203 through a variety of known techniques, such as, but not limited to, epoxy or spot welding.

Figure 5:
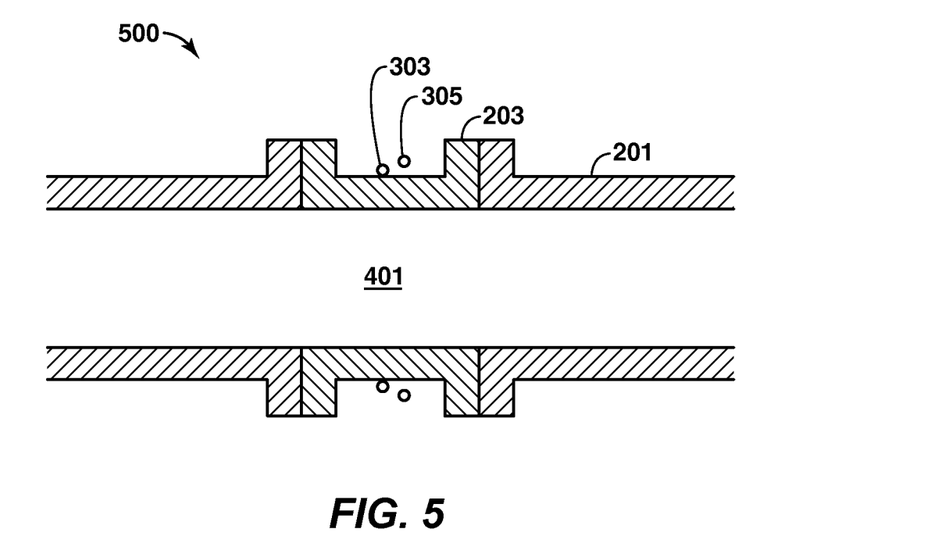
FIG. 5 is a cross-sectional side view of a pipeline sensor system according to an embodiment of the present disclosure.

Non-corrosive base 203 is constructed and arranged to maintain a fixed base geometry over time; thus, the relationship between pressure, temperature and strain will be maintained identical over time. As depicted, sensing module 205 contains two fiber optic sensing elements 303, 305. Sensing element 303 is provided in such a way to touch base portion 207. FIG. 5 is a cross-sectional side view of a pipeline sensor system 500 according to an embodiment of the present disclosure. As depicted, the inner region of pipeline 201 is generally depicted by reference numeral 401. The FIG. 5 embodiment does not include base portion 207. Therefore, any support structures 301 for the fiber optic sensors 303, 305 are provided directly to non-corrosive base 203. Sensing element 303 may directly touch non-corrosive base 203.

As depicted, sensing element 305 is positioned in close proximity to the base portion 207 without touching it. Alternatively, sensing element 305 may touch non-corrosive base 203 or base portion 207. By touching base portion 207 which is directly connected to the exterior surface of non-corrosive base 203 (or by touching the exterior of non-corrosive base 203 directly as in the FIG. 5 embodiment), sensing element 303 measures the strain caused by the internal pressure and temperature ($\epsilon_P+\epsilon_T$) of the pipe or vessel.

Sensing element 305 is used to measure temperature. Based on the measured temperature, the strain induced by temperature ($\epsilon_T$) can be determined Given these two measurements, the strain induced by pressure can be calculated accordingly. Based on the relationship between pressure, temperature and strain, the internal pressure and temperature of the pipe or vessel can be calculated accordingly to known principles. Additional sensing elements may be utilized to provide redundancy. The specific methodologies, techniques and components used to measure strain and temperature with fiber optic cable is understood by those skilled in the art.

Figure 6:
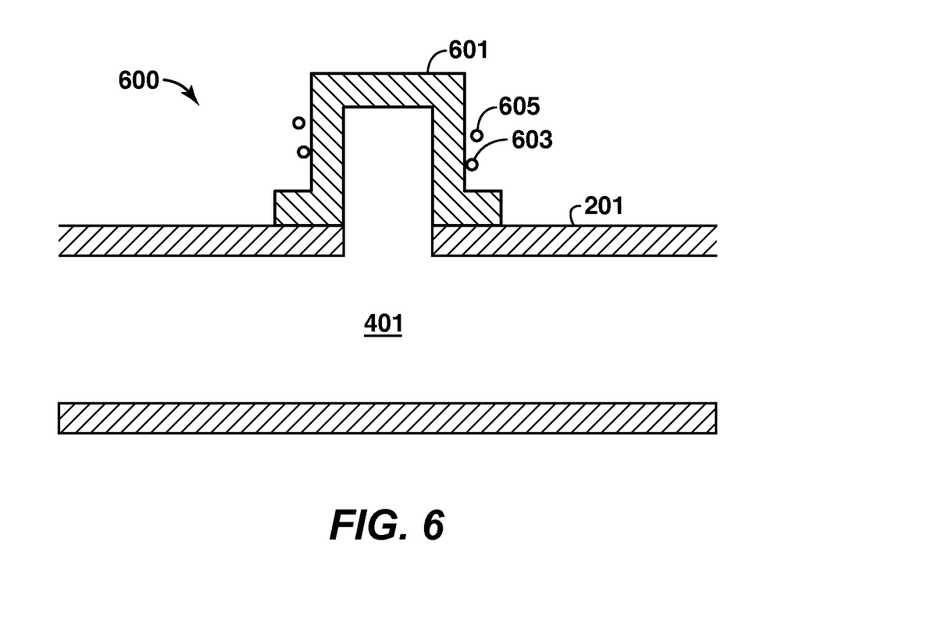
FIG. 6 is a cross-sectional side view of a pipeline sensor system according to a further embodiment of the present disclosure.

FIG. 6 is a cross-sectional side view of a pipeline sensor system 600 according to a further embodiment of the present disclosure. Like system 200 of FIG. 2, system 600 contains a pipeline 201 and a non-corrosive base 601 which is provided a various locations along pipeline 201. Unlike system 200, non-corrosive base 601 is not provided in-line with pipeline 201. Instead, non-corrosive base 601 is attached to the outer surface of pipeline 201 proximate to an aperture provided in pipeline 201. As depicted, the inner region defined by the internal surface of base 601 is communicatively connected to the inner region of the pipeline which is generally depicted by reference numeral 401. As described herein, measurement provided by fiber optic sensors 603, 605 may lead to the determination of the pressure and temperature of the pipeline or other vessel. Pipeline sensor system 600 may utilize a base portion similar to the one depicted in FIG. 2.

As described herein, the pipeline sensor systems of the present disclosure utilize subsea external fiber optic PT sensor designs. Such designs may exhibit an array of benefits, such as, but not limited to, long term stability, high reliability, low cost redundancy, easy replacement, etc. The sensor modules of the present disclosure may be easily retrieved by an ROV, to name one example. Because the non-corrosive base stays in position in the event a sensor module is removed, it is not necessary to stop the fluid flow through the pipeline or other vessel in the event a sensor module needs to be serviced.

Figure 7:
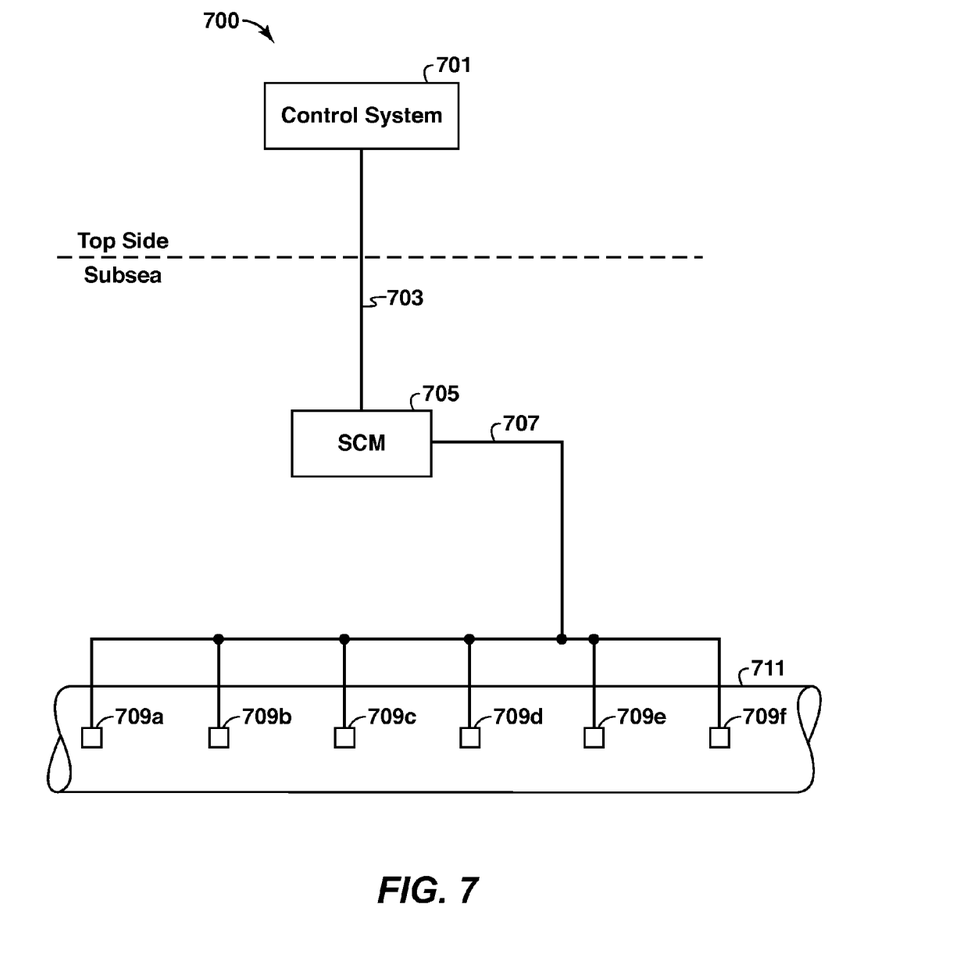
FIG. 7 is a block diagram of a pipeline system according to an embodiment of the present disclosure.

FIG. 7 is a block diagram of a pipeline system 700 according to an embodiment of the present disclosure. As depicted, a topside operations and control system 701 is connected to a subsea control module (SCM) 705 via an umbilical 703. Umbilical 703 may be constructed and arranged to provide fiber optics, power, fluids, etc. to SCM 705. SCM 705 can then provide the appropriate fiber optic signals to a variety of fiber optic sensor modules 709a-709f provided along a pipeline 711.

Operations and control system 701 may be provided with a broad spectrum laser source. The broad spectrum laser then communicated to sensor modules 709a-709f via umbilical 703, SCM 705 and communication line 707. Though each sensor module 709a-709f receives the broad spectrum, each sensor module may be energized by a specific frequency band. After the return signal has been received, the pertinent sensor location can be identified based on the frequency and the temperature and pressure of the pipeline at that location may be calculated based on the measured strains.

Figure 8:
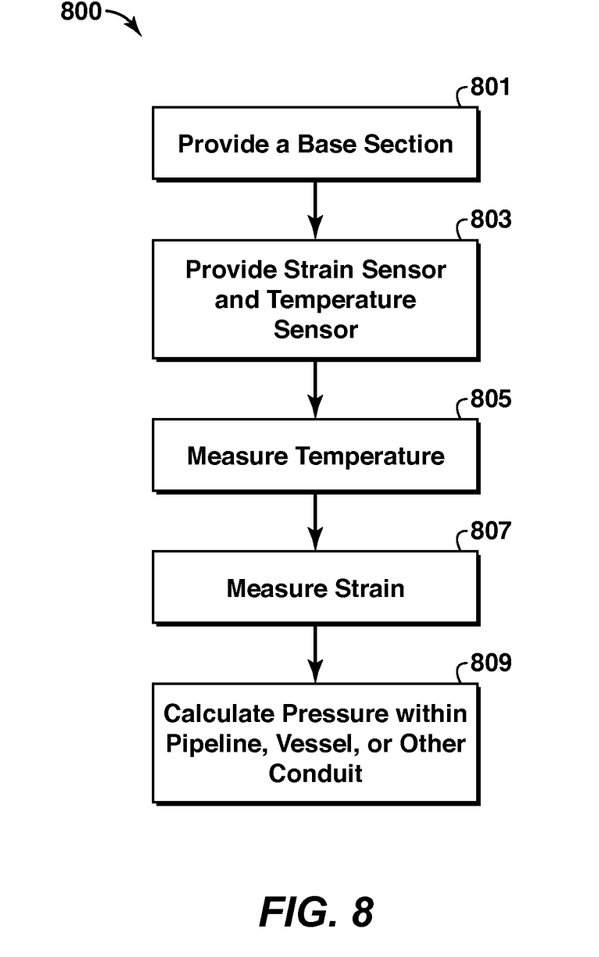
FIG. 8 is a flowchart showing the basic steps of determining a pressure within a conduit according to an embodiment of the present disclosure.

The flowchart of FIG. 8 will be referred to in describing one embodiment of the present disclosure for non-intrusively determining a pressure within a pipeline, vessel or other conduit. The depicted process 800 begins by providing a base section having an internal region in fluid connection with the conduit (step 801). A strain sensor and a temperature sensor are also provided (step 803). As described herein, the strain sensor and the temperature sensor are positioned adjacent to an external surface of the base section. The temperature sensor is used to measure the temperature of the pipeline, vessel or other conduit (step 805). The strain sensor measure is used to measure a strain exhibited on the pipeline, vessel or other conduit (step 807). The measured strain is based on an internal pressure of the conduit and the temperature of the pipeline or conduit. At step 809, the pressure within the conduit can be calculated. The pressure calculation is based upon the measured temperature and the measured strain.

The process for determining pressure may include calculating a strain due to temperature based upon the measured temperature. The process for determining pressure may include calculating a strain due to pressure based upon the measured strain due to pressure and temperature and the calculated strain due to temperature. The calculation of the pressure within the conduit may then be based upon the calculated strain due to pressure.

The sensor modules may include a protective housing to surround the fiber optic components. The fiber optic components may be encapsulated in a resin or similar material. While the systems depicted in FIGS. 4-6 show two sensor modules at a given pipeline location, any number of sensor modules may be used in order to provide the desired amount of specificity with respect to temperature and pressure measurements. While the present disclosure makes reference to subsea components, the sensor modules described herein may be equally applied to land-based pipelines and other vessels.

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional blocks not shown herein. While the figures illustrate various actions occurring serially, it is to be appreciated that various actions could occur in series, substantially in parallel, and/or at substantially different points in time.

It should be understood that the preceding is merely a detailed description of specific embodiments of this invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

What is claimed is:

1. A method for non-intrusively determining a pressure within a conduit comprising:
    providing a base section having an internal region in fluid connection with the conduit, wherein the base section is made of a non-corrosive alloy;
    providing a strain sensor and a temperature sensor which are positioned adjacent to an external surface of the base section;
    measuring a temperature with the temperature sensor;
    measuring a strain with the strain sensor, said strain is based on an internal pressure of the conduit and the temperature of the conduit, wherein at least one of the strain sensor and temperature sensor are comprised of fiber optics; and
    calculating a pressure within the conduit based upon the measured temperature and the measured strain.

2. The method of claim 1 further comprising calculating a strain due to temperature based upon the measured temperature.

3. The method of claim 2 further comprising calculating a strain due to pressure based upon the measured strain due to pressure and temperature and the calculated strain due to temperature.

4. The method of claim 3, wherein the calculating the pressure within the conduit is based upon the calculated strain due to pressure.

5. The method of claim 1, wherein both of the strain sensor and temperature sensor are comprised of fiber optics.

6. The method of claim 1, wherein the non-corrosive alloy is selected from the group consisting of titanium, Alloy 13 Cr, Alloy S13 Cr, Alloy 316L, Alloy 22 Cr duplex, Alloy 25 Cr duplex, Alloy 28, Alloy 825, Alloy 2550, Alloy 625, and Alloy C-276.

7. A system for non-intrusively determining pressure comprising;
    a conduit;
    a base section having an external surface and an internal region in fluid connection with the conduit, wherein the base section is made of a non-corrosive alloy;
    a strain sensor positioned adjacent to the external surface of the base section to measure strain based on an internal pressure of the conduit and a temperature of the conduit; and
    a temperature sensor positioned adjacent to the external surface of the base section, wherein at least one of the strain sensor and temperature sensor are comprised of fiber optics.

8. The system of claim 7, wherein the strain sensor is constructed and arranged to touch the external surface of the base section.

9. The system of claim 7 further comprising a mounting portion affixed to the external surface of the base section, wherein the strain sensor and the temperature sensor are connected to the mounting portion.

10. The system of claim 7, wherein both of the strain sensor and temperature sensor are comprised of fiber optics.

11. The system of claim 7, wherein the non-corrosive alloy is selected from the group consisting of titanium, Alloy 13 Cr, Alloy S13 Cr, Alloy 316L, Alloy 22 Cr duplex, Alloy 25 Cr duplex, Alloy 28, Alloy 825, Alloy 2550, Alloy 625, and Alloy C-276.

12. The system of claim 7, wherein the temperature sensor is radially offset from the external surface of the base section.

13. The system of claim 7, wherein the base section is provided in-line with the conduit.

14. The system of claim 7, wherein the conduit has an aperture and an outer surface, the base section is affixed to the outer surface proximate to the aperture, the aperture allows for the fluid connection between the internal region of the base section and the conduit.

* * * * *